(12) United States Patent
Burchett et al.

(10) Patent No.: US 6,502,608 B1
(45) Date of Patent: Jan. 7, 2003

(54) DELIVERY APPARATUS, NOZZLE, AND REMOVABLE TIP ASSEMBLY

(75) Inventors: Ronnie Burchett, Missoula, MT (US); Randy Scot Wills, Florence, MT (US)

(73) Assignee: Telios Orthopedic Systems, Inc., Missoula, MT (US)

( * ) Notice: Subject to any disclaimer, the term of this patent is extended or adjusted under 35 U.S.C. 154(b) by 0 days.

(21) Appl. No.: 09/503,947

(22) Filed: Feb. 14, 2000

(51) Int. Cl.⁷ .......................... B65B 39/00; B67C 11/04
(52) U.S. Cl. ...................... 141/386; 141/383; 141/384; 141/391; 141/392; 604/82; 606/92
(58) Field of Search ................................ 141/383, 384, 141/386, 387, 391, 392; 222/136, 137, 229, 233–235, 260, 278, 280, 390; 604/82, 218, 224, 228; 606/92, 93; 285/361, 376, 906

(56) References Cited

U.S. PATENT DOCUMENTS

| | | | |
|---|---|---|---|
| 4,466,435 A | 8/1984 | Murray | 128/303 R |
| 4,671,263 A * | 6/1987 | Draenert | 128/92 |
| 5,265,956 A | 11/1993 | Nelson et al. | 366/139 |
| 5,344,232 A | 9/1994 | Nelson et al. | 366/139 |
| 5,415,474 A | 5/1995 | Nelson et al. | 366/139 |
| 5,431,654 A | 7/1995 | Nic | 606/92 |
| 5,466,020 A * | 11/1995 | Page et al. | 285/361 |
| 5,545,460 A | 8/1996 | Tanaka et al. | 428/137 |
| 5,558,136 A | 9/1996 | Orrico | 141/23 |
| 5,588,745 A | 12/1996 | Tanaka et al. | 366/130 |
| 5,842,785 A | 12/1998 | Brown et al. | 366/139 |
| 6,238,399 B1 * | 5/2001 | Heller et al. | 606/92 |

\* cited by examiner

Primary Examiner—Timothy L. Maust
(74) Attorney, Agent, or Firm—Dorsey & Whitney LLP

(57) ABSTRACT

A bone cement delivery apparatus is provided. The delivery apparatus includes a delivery tube and a connector. The delivery tube has an inner wall providing an axial bore. The connector is provided at a proximal end of the delivery tube. The connector includes at least one receiving slot in the inner wall. The receiving slot includes a transverse portion comprising an override surface and a local recess which cooperate to removably mate the delivery tube and the connector with a bone cement dispensing apparatus.

27 Claims, 7 Drawing Sheets

DELIVERY APPARATUS, NOZZLE, AND REMOVABLE TIP ASSEMBLY

TECHNICAL FIELD

This invention pertains in general to bone cement dispensing and delivery apparatus for flowable materials. More particularly, this invention relates to dispensing tips and nozzles for use in conjunction with a dispensing apparatus or container for binding materials such as surgical bone cement.

BACKGROUND OF THE INVENTION

Reconstructive bone surgery is a common procedure to replace bone structures. For example, replacement hip surgery uses a prosthetic hip joint to replace a patient's hip joint. Such surgical procedures include removing the hip joint from a femur, packing bone cement within an inner canal of the femur, and positioning the prosthetic hip joint into the bone cement inside the femur. Subsequently, the cement is allowed to harden, thereby securing the hip joint in place. A tip that is secured to a bone cement dispensing apparatus or container is commonly used to issue bone cement into a bone canal of the femur.

For example, to apply bone cement, the bone canal is cleaned out and the dispensing tip is introduced into the canal extending to a distal end of the canal which has previously been blocked with a canal plug. As bone cement issues from the tip into the canal, the tip is withdrawn from adjacent the canal plug in a retrograde fashion to the proximal end of the canal, thereby filling the canal with cement.

One technique to enhance filling of the proximal end of the bone canal is to shorten the tip, after first filling the proximal end, by snapping off an end of the tip using a score line provided for this purpose. However, this technique has disadvantages. First, snapping off the end can leave particulates of the tip structure in the surgical area and on the newly shortened end of the tip. When the tip is reintroduced into the canal to finish filling the proximal end of the bone canal, the particulates can contaminate the surgical site. The contamination can lead to infection in the bone and/or weakening of the bone cement once the cement hardens. Secondly, even the best score line can leave minute jagged edges after the tip end is broken away. Such jagged edges can cause injury to canal tissue upon reintroducing the tip in the bone, or can cut through protective surgical gloves used by surgical personnel during manipulation of the bone cement dispensing apparatus and delivery tip. In the latter case, a health risk is presented to the personnel, such as a risk of transmitting acquired immune deficiency syndrome (AIDS).

Typically, for the case of a bone cement delivery system having multiple interchangeable tips, a single tip is sealed in a package and stored in an area which may not be as sterile as the surgical room. Before or during the surgical procedure, a surgical nurse or assistant makes a determination as to the size of tip needed and secures the tip to a bone cement dispensing container, typically by threaded cooperation, either in the surgical room or in a less sterile environment. If during the surgical procedure a different sized tip is needed, the surgical nurse/assistant then has to venture to the less sterile area in order; to retrieve another tip and then rethread the new tip onto the cement dispensing container. The retrieval of another tip by personnel wastes time where time is typically important because bone cement is relatively fast setting and a predetermined time frame is provided by the bone cement in which a surgical procedure has to be performed, else the bone cement hardens and is wasted. Since bone cement is expensive, it is important that any delays (expected or unexpected) be minimized once the bone cement has been prepared. Additionally, for the case where a nurse/assistant is required to leave the sterile environment of a surgical room in order to retrieve a different tip, potential for contamination of the surgical area is increased.

Therefore, there exists a need for an improved bone cement delivery apparatus, including a tip, to be used with bone cement dispensing apparatus or containers, a need to provide access to a plurality of tips each with unique dimensions suited for a particular use, and a single, common nozzle, and a need for the tips to be located in the most sterile environment possible.

SUMMARY OF THE INVENTION

One or more tips are constructed for use in a bone cement delivery apparatus. The tips are quickly and easily attached and detached from a bone cement dispensing apparatus, or container. A bone cement delivery apparatus includes one or more interchangeable tubular dispensing tips and a dispensing apparatus, or container. Additionally, the delivery apparatus can include a nozzle that communicates with the bone cement dispensing apparatus. According to one construction, the dispensing tip and nozzle are removably secured together with a pair of complementary, mating connectors. According to other aspects, a plurality of individually unique, such as variously sized; dispensing tips, are interchangeably mated with a single, common nozzle. Each tip has a delivery tube and a connector, and according to one construction, the connector is integrally formed from the delivery tube. According to one package configuration, the tips are stored in a first hermetically sealed tub that is removable from a second hermetically sealed tub.

According to one aspect, a bone cement delivery apparatus is provided. The delivery apparatus includes a delivery tube and a connector. The delivery tube has an inner wall providing an axial bore. The connector is provided at a proximal end of the delivery tube. The connector includes at least one receiving slot in the inner wall. The receiving slot includes a transverse portion comprising an override surface and a local recess which cooperate to removably mate the delivery tube and the connector with a bone cement dispensing apparatus.

According to another aspect, a fluent material delivery apparatus is provided. The delivery apparatus includes a tip and a nozzle. The tip has a delivery tube and a delivery tube connector. The delivery tube connector includes at least one receiving slot provided in the delivery tube, and having a transverse portion including an override surface and a local recess. The nozzle has a nozzle connector. The nozzle communicates with a fluent material dispensing apparatus, and the nozzle connector is configured to removably mate with the delivery tube connector. The nozzle connector includes at least one node sized for slidable engagement with the receiving slot. The node is operative to mate in interlocking engagement with the local recess of the transverse portion responsive to circumferential manipulation of the nozzle and the at least one node over the override surface of the at least one receiving slot.

According to yet another aspect, a nozzle is provided for connecting a delivery tube with a bone cement dispensing apparatus. The nozzle includes a first portion and a second portion. The first portion has an outer surface configured to be received in a delivery tube. The outer surface defines at least one node configured to secure the delivery tube in interlocking engagement with the nozzle. The second portion communicates with the supply of bone cement.

According to even another aspect, a removable tip assembly is provided in conjunction with a bone cement dispenser. The removable tip assembly includes a converging section, a cylindrical portion, and a tubular body. The cylindrical portion integrally extends from a smaller diameter of the converging section. The cylindrical portion comprises an outer wall defining an aperture. The tubular body has: a proximal and a distal end. The proximal end integrally extends from the cylindrical portion to the distal end. The converging section, the cylindrical portion, and the tubular body define an axial bore, and the aperture of the cylindrical portion extends through the outer wall to the axial bore.

BRIEF DESCRIPTION OF THE DRAWINGS

Preferred embodiments of the invention are described below with reference to the following accompanying drawings depicting examples embodying the best mode for practicing the invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts"(Article 1, Section 8).

Reference will now be made to a preferred embodiment of Applicant's invention. One exemplary implementation is described below and depicted with reference to the drawings. While the invention is described via a preferred embodiment, it is understood that the description is not intended to limit the invention to this embodiment, but is intended to cover alternatives, equivalents, and modifications such as are included within the scope of the appended claims. For example, this invention can be used to deliver any material having fluent properties during delivery, whether such material remains fluent or not after application.

Figure 1:
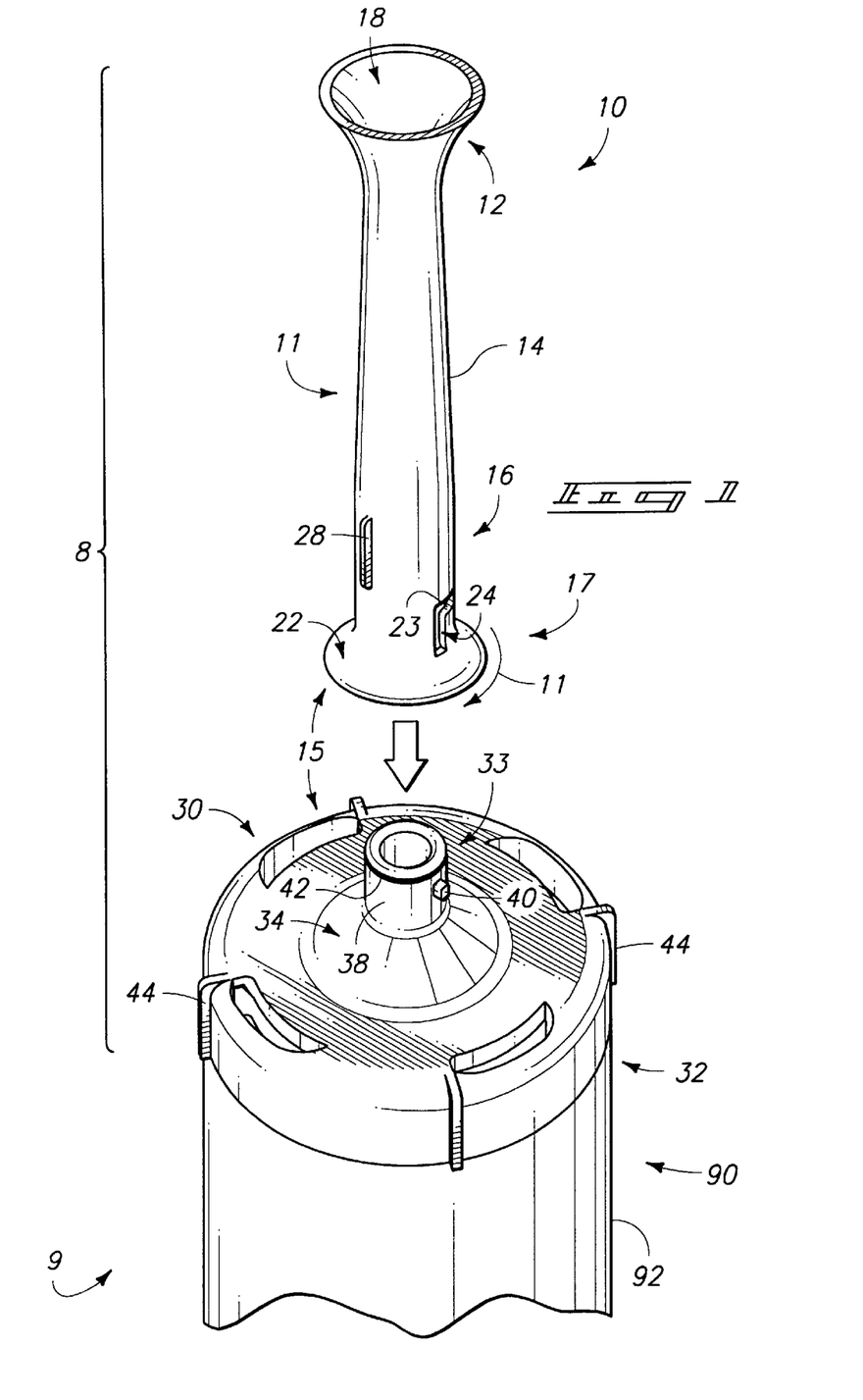
FIG. 1 is a perspective view of a tip and a nozzle, and a partial view of a bone cement dispensing apparatus, or container, with the nozzle secured onto the container and the tip positioned for releasable securement to the nozzle according to one aspect of the invention.

FIG. 1 illustrates an exploded perspective view of a tubular dispensing tip, generally indicated by reference numeral 10, shown positioned above a nozzle, generally indicated by reference numeral 30, and readied for attachment according to one aspect of the invention. Nozzle 30 is shown secured to a bone cement dispensing apparatus, or container, 90 (container 90 is shown in partial view) configured to dispense a surgical bone cement such a methyl methacrylate.

As shown in FIG. 1, tip 10 and nozzle 30 cooperate to provide a bone cement delivery apparatus 8. Bone cement delivery apparatus 8 comprises a removable tip assembly that cooperates with bone cement dispensing apparatus 90 to form a bone cement delivery system 9. Tip 10 includes a delivery tube 11 having a proximal end 16, a distal end 12, and an axial bore 18 extending between the proximal end 16 and the distal end 12. Delivery tube 11 has a tubular outer wall 14 and a tubular inner wall 19.

Tip 10 is mated to and demated from nozzle 30 via a quick connect/disconnect connector assembly 15. Connector assembly 15 includes a delivery tube connector 17 provided on delivery tube 11 of tip 10 and a nozzle connector 33 provided on nozzle 30. Connector assembly 15 facilitates quick and efficient attachment of a selected tip 10 onto a source of bone cement such as a bone cement dispensing apparatus 90. Accordingly, the risk that bone cement will be wasted due to delays in preparing and delivering such cement to a patient is greatly reduced. Additionally, desirable locking and sealing features are provided by connector assembly 15, as described below in greater detail.

Proximal end 16 on delivery tube 11 provides for integrally formed delivery tube connector 17, including a pair of securement (or receiving) slots 23 which define apertures 24. Furthermore, proximal end 16 terminates in a frustoconical end portion 22 which facilitates insertion of a tubular section 38 of nozzle connector 33 within delivery tube connector 17. A pair of opposed ridges 28 are provided on tubular outer wall 14 to facilitate tactile rotatable locking engagement between delivery tube connector 17 and nozzle connector 33.

Nozzle 30 includes a first cap portion 32 and a second cap portion 34. As will be described below in greater detail, first cap portion 32 is removably mated with a bone cement containment/delivery tube 92 of bone cement dispensing apparatus, or container, 90. Nozzle connector 33 is provided on second cap portion 34. A pair of nodes, or projecting fingers, 40 extend radially outwardly from tubular section 38 of nozzle connector 33 for interdigitating engagement within retaining slots 23. A circumferential seal 42 formed about tubular section 38 seals tip 10 with nozzle 30 when joined together.

Figure 2:
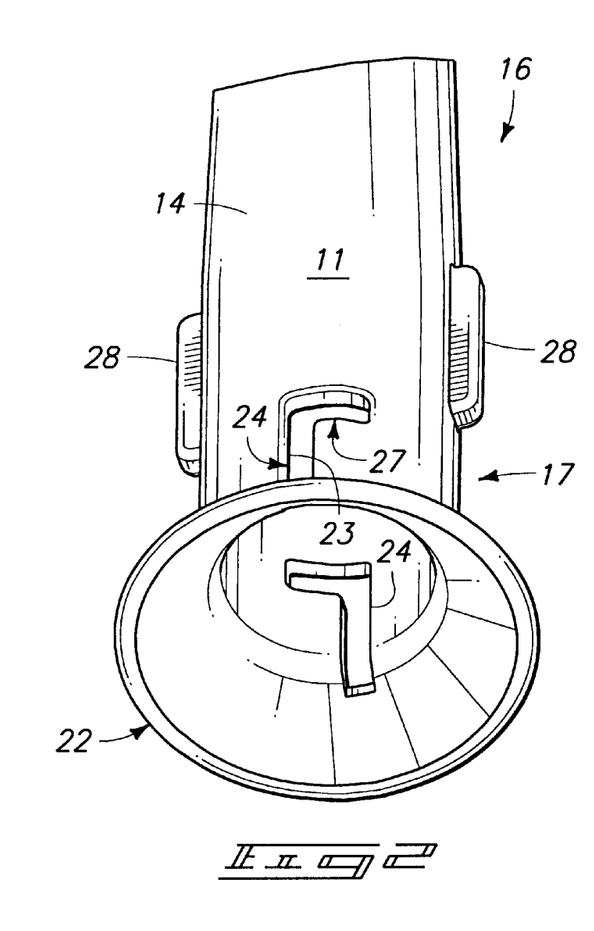
FIG. 2 is a perspective view of a proximal end of the tip of FIG. 1.

FIG. 2 illustrates proximal end 16 of delivery tube 11 which includes outwardly flared frustoconical portion 22. A converging diameter of frustoconical portion 22 is integrally formed with delivery tube 11. Tubular outer wall 14, along proximal end 16, defines two diametrically opposed securement slots 23 which, in one embodiment, form apertures 24 in delivery tube 11 extending between tubular outer wall 14 and an inner wall 19 that defines axial bore 18.

Two diametrically opposed ridges 28 extend radially outwardly from tubular outer wall 14. According to one aspect, ridges 28 are circumferentially displaced from apertures 24 and are axially closer to the distal end 12 of delivery tube 11 than are apertures 24.

Figure 3:
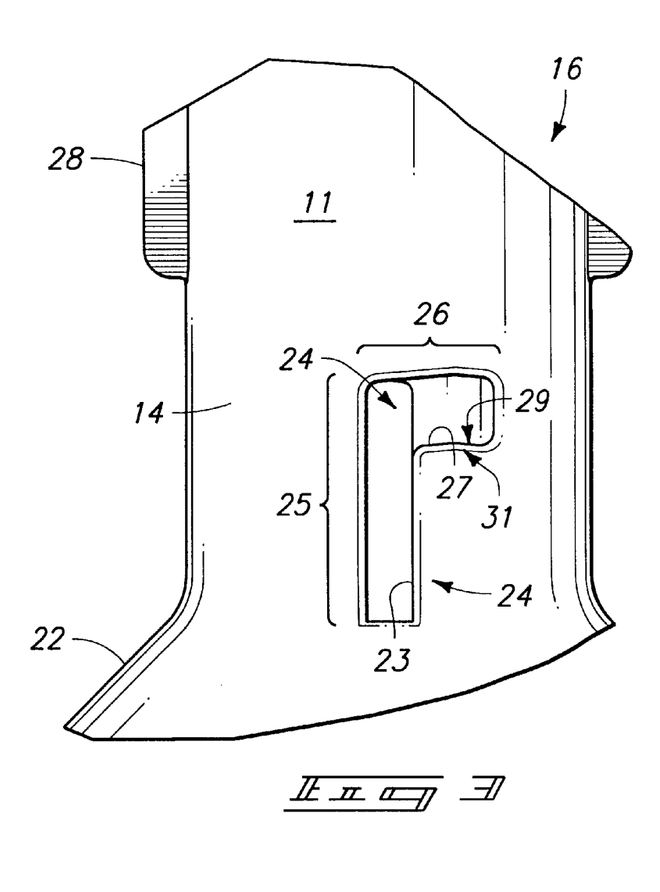
FIG. 3 is a partial side view of the tip of FIGS. 1 and 2 showing one of the securement openings.

FIG. 3 illustrates one of the apertures 24 present within proximal end 16. Aperture 24 represents one envisioned embodiment of securement (or retaining) slot 23. Although securement slot 23 is implemented in the form of aperture 24, it is understood that aperture 24 can be constructed such that a slot is provided along the inner wall 19 so as to not extend all the way through delivery tube 11. Securement slot 23 (in this case aperture 24) has a longitudinally extending portion 25 and a circumferentially extending portion 26. Both portions combine to form a continuous aperture 24 generally shaped as "r" with the circumferentially extending portion 26 at an end of the longitudinally extending portion 25 closest to the distal end 12 of tip 10.

As shown in FIGS. 2 and 3, delivery tube connector 17 comprises a female connector formed from proximal end 16 of delivery tube 11. According to one construction, a pair of diametrically opposed securement, or receiving, slots 23 are provided by delivery tube connector 17 so as to each define a respective aperture 24. It should be appreciated that aperture 24 includes longitudinally extending portion 25 which extends toward the right from the perspective view in FIG. 3. As shown in FIG. 2, each aperture 24 is configured with transverse, or circumferentially extending, portion 26 extending from the right of longitudinally extending portion 25, as viewed from the outer surface of delivery tube 11.

As shown in FIG. 3, circumferentially extending portion 26 of aperture 24 has a proximal edge 27 that is raised slightly to form an override surface so as to axially extend toward distal end 12 of tip 10. However, a local recess 29 is provided adjacent proximal edge 27 which lowers slightly to axially extend in a direction away from distal end 12 of tip 10.

Circumferentially extending portion 26 comprises a transverse portion having a cam surface 31 which forms the override surface and includes proximal edge 27 and local recess 29. Local recess 29 is provided proximally closer to the proximal end 16 than is proximal edge 27 in order to ensure positive securement of tip 10 to nozzle 30 (see FIGS. 8 and 9).

According to the construction depicted in FIG. 3,; securement slot 23 defines aperture 24 which includes a biasing portion or edge, comprising cam surface 31. Cam surface 31 includes proximal edge 27 and local recess 29. Cam surface 31 defines a sliding machine surface formed within an aperture, groove or slot and having a shape that imparts motion to a follower which is variable, and in many cases complex. According to the construction depicted in FIG. 3 (and later detailed in FIGS. 8 and 9), a node 40 (see FIGS. 8 and 9) engages against cam surface 31 so as to act as a follower which is urged in interlocking engagement within local recess 29.

Figure 4:
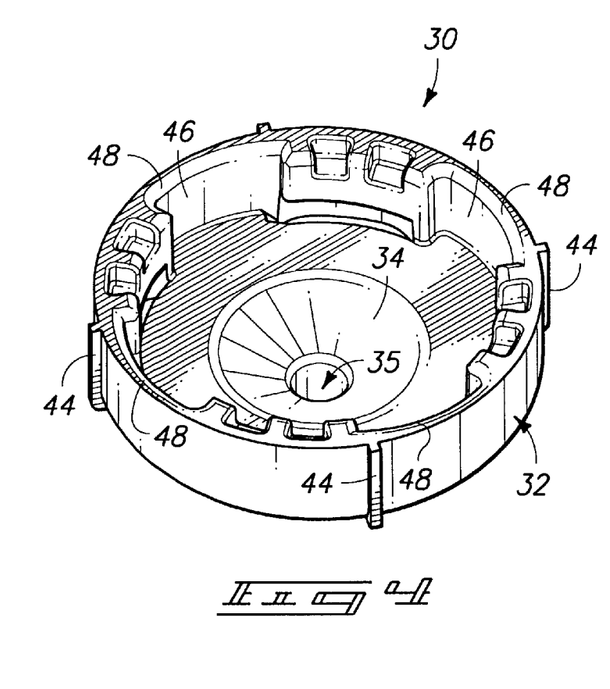
FIG. 4 is a perspective bottom view of the nozzle of FIG. 1.
Figure 5:
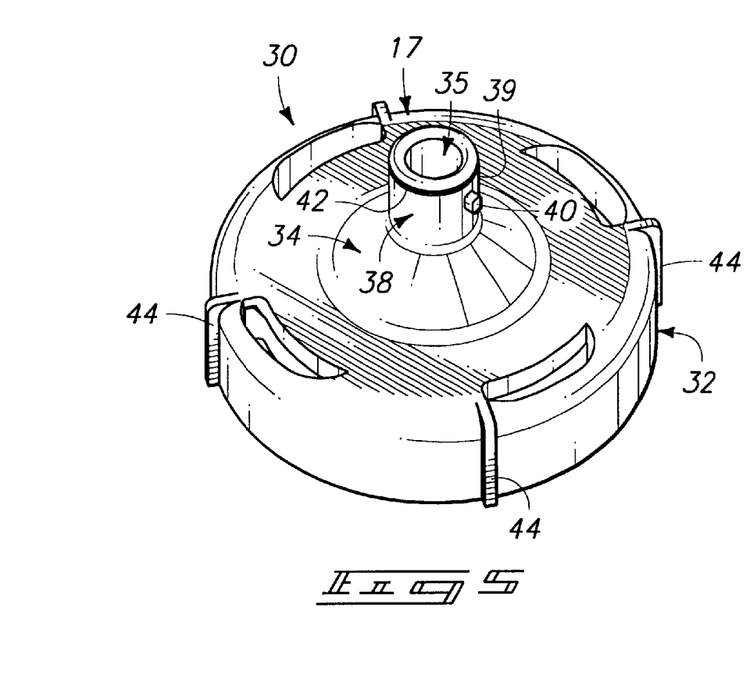
FIG. 5 is a perspective top view of the nozzle of FIGS. 1 and 4.

FIGS. 4–5 illustrate nozzle 30 that interconnects and removably mates with tip 10 so as to join tip 10 with bone cement dispensing apparatus, or container, 90, thereby providing fluid communication between tip 10 and container 90. Nozzle 30 comprises a first cap portion 32 designed to be removably received on container 90. (FIG. 1) as a removable cap. First cap portion 32 is generally. cylindrical with a plurality of radially extending ridges 44 (also see FIG. 1).

Referring to FIG. 4, inside first cap portion 32 are carved out regions 46 that have tapered edges 48 to provide a resistance fit over container 90 upon finger manipulation of ridges 44 to twist the nozzle 30 onto an end of container 90.

Details of the manner in which nozzle 30 is mated and demated with container 90 (of FIG. 1) are disclosed in Applicant's co-pending U.S. patent application Ser. No. 9/503,877 now U.S. Pat. No. 6395006, entitled "Connector Assembly for Mating Components, Connector Assembly for a Bone Mixing and Delivery System, and Bone Cement Container Having a Connector Assembly", naming the inventor as Ronnie Burchett, and filed concurrently herewith. Such U.S. patent application Ser. No. 09/503,877 is herein incorporated by reference as evidencing one manner in which to secure nozzle 30 to container 90. Optionally, nozzle 30 can be threaded onto container 90 using complementary threaded portions, each having threads. Even further optionally, nozzle 30 can be integrally formed from one end of container 90.

Referring to FIG. 5, nozzle 30 includes a second cap portion 34 integrally extending from the first cap portion 32. The second cap portion 34 comprises a tubular section 38 defining an inner axial bore 35 and an outer cylindrical surface 39. Outer cylindrical surface 39 is dimensioned with a smaller diameter than the diameter of axial bore 18 at the proximal end 16 of tip 10 to facilitate positioning therein.

Figure 6:
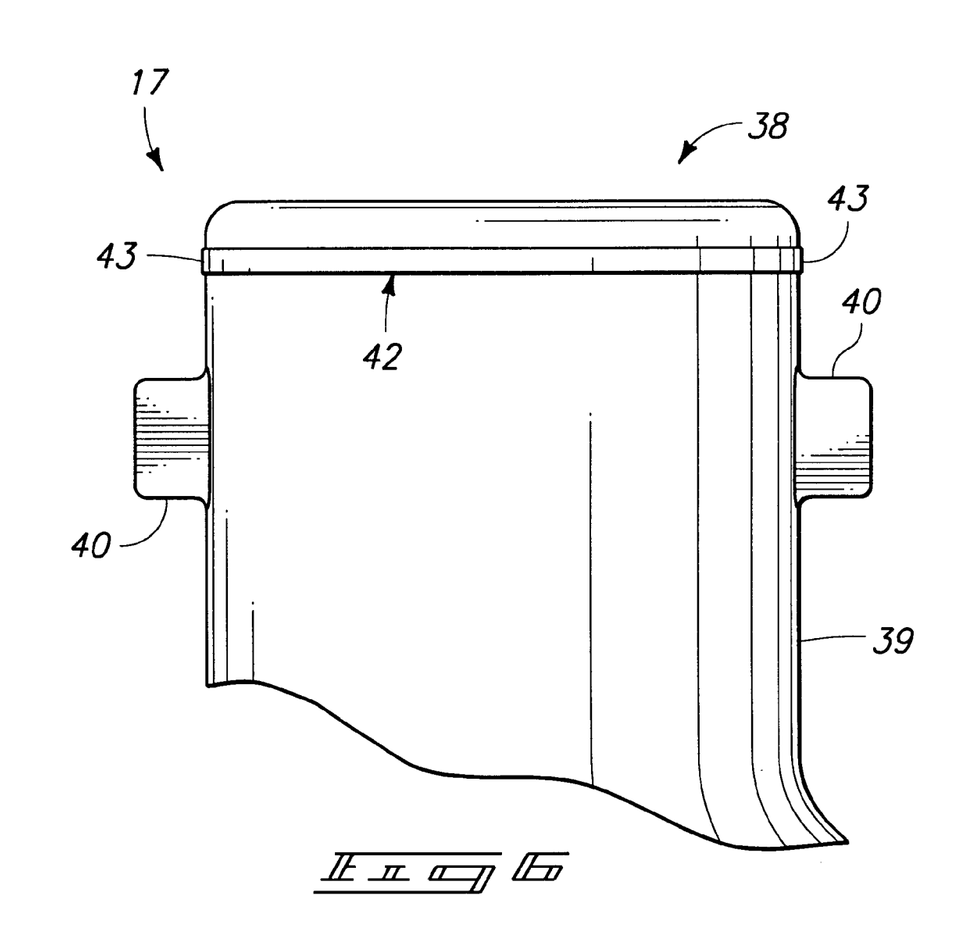
FIG. 6 is a partial view of the nozzle of FIGS. 1, 4 and 5 showing a tubular section or portion that is received within the distal end of the tip as shown in FIG. 1.

FIG. 6 illustrates an enlarged view of tubular section 38 of nozzle 30. A pair of diametrically opposed nodes 40 extend from the outer cylindrical surface 39. A circumferential seal 42 is integrally formed from outer cylindrical surface 39 where seal 42 extends about the entire outer periphery of surface 39. Seal 42 is sized so as to provide an interference surface 43 that, in assembly, seats in sealing engagement with an inner sealing surface 45 as nodes 40 are fully engaged within securement openings 24.

Figure 7:
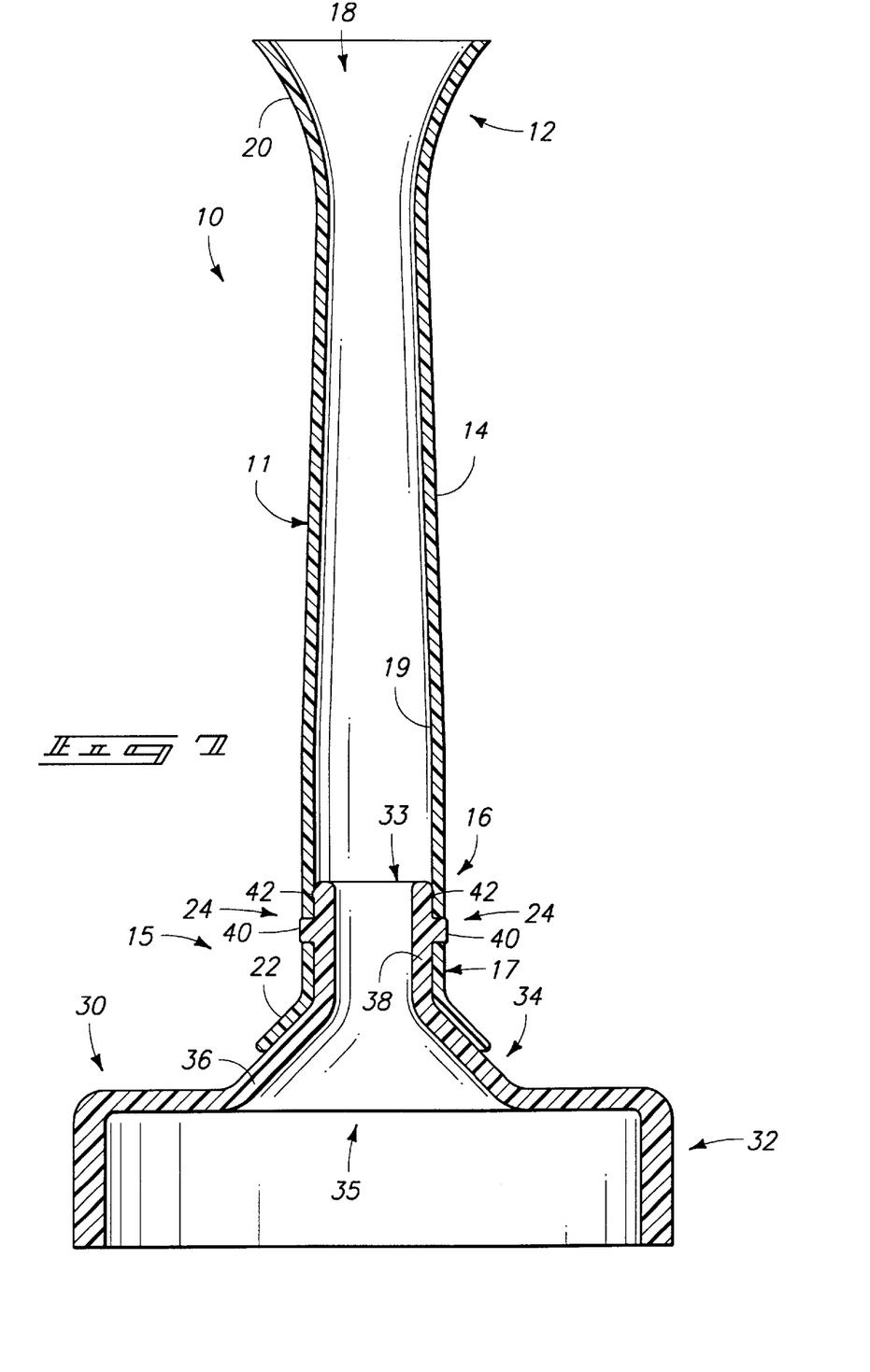
FIG. 7 is a longitudinal and centerline sectional view of the tip and nozzle with the tip secured to the nozzle.

FIG. 7 illustrates a sectional view of tip 10 secured to nozzle 30. Axial bore 18 of proximal end 16 is contoured so as to receive second portion 34 of nozzle 30. Nodes 40 are positioned in openings 24 of tip 10 to lock nozzle 30 and tip 10 together. Interference surface 43 (FIG. 6) of circumferential seal 42 contacts sealing surface 45 at axial bore 18 to fluidly seal nozzle 30 to tip 10. Axial bore 18 of tip 10 and inner axial bore 35 of nozzle 30 provide fluid communication between tip 10 and bone cement container 90. Pursuant to one aspect, circumferential seal 42 provides an interference surface 43 approximately .0025 inches above, or radially outwardly of, the outer cylindrical surface 39.

Figure 8:
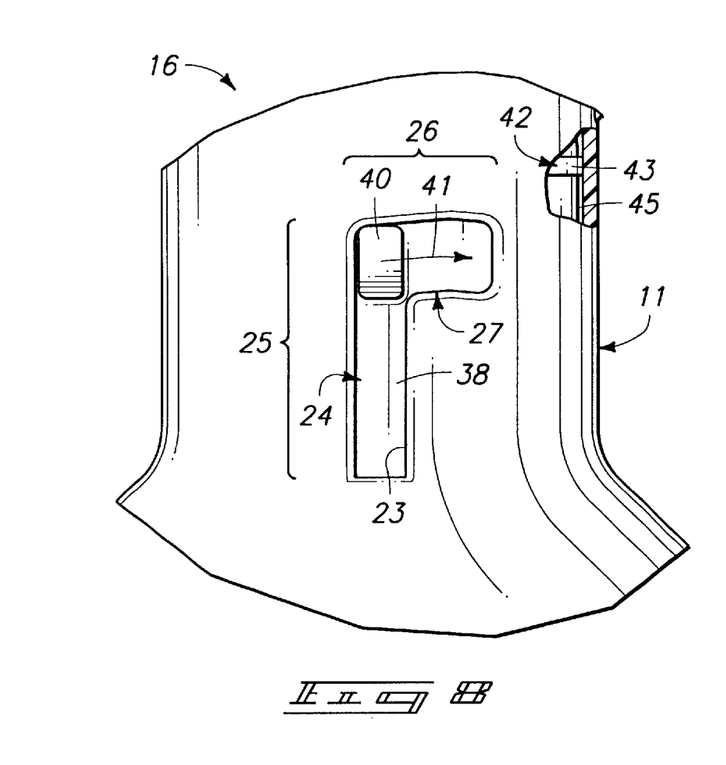
FIG. 8 is a partial view of the proximal end of the tip showing a node on the nozzle inserted into a corresponding securement opening in the tip prior to locking the tip onto the nozzle by rotating the tip relative to the nozzle.
Figure 9:
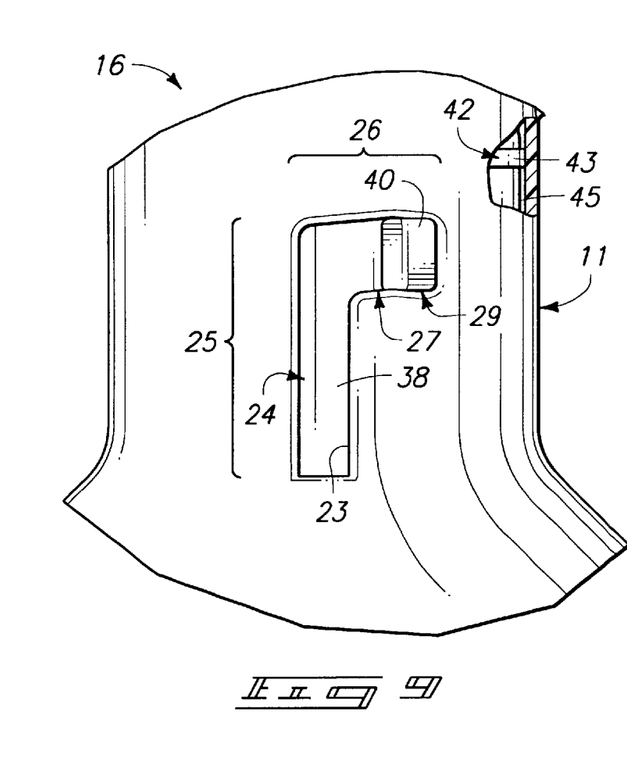
FIG. 9 is a view similar to FIG. 8 showing the tip locked onto the nozzle after fully engaging the node within the securement slot, or aperture, by rotating the tip with respect to the nozzle.

FIGS. 8–9 illustrate releasably locking cooperation between tip 10 and nozzle 30. Referring to FIG. 8, as tip 10 and nozzle 30 are positioned for connection, axial bore 18 of tip 10 is provided axially over the tubular portion 38 with node 40 engaging the longitudinally extending portion 25 of opening 24. Nodes 40 move axially along longitudinally extending portion 25 toward distal end 12 of tip 10 until nodes 40 engage the respective circumferentially extending, or transverse, portions 26. Next, tip 10 and/or nozzle 30 are rotated relative one another in opposite directions to move nodes 40 into the respective circumferentially extending portion 26 as indicated by direction arrow 41. According to one aspect, tip 10 would be rotated in a clockwise motion 11 as shown in FIG. 1.

Referring to FIG. 9, node 40 moves into circumferentially extending portion 26 over proximal edge 27. Proximal edge 27 acts to bias or cam the node 40 toward the distal end 12 of tip 10, thereby forcing tip 10 and nozzle 30 together in a locking manner. It should be understood that another node 40 and an opening 24 are interacting in the same manner on opposite sides of nozzle 30 and tip 10, respectively.

As nodes 40 pass over each respective proximal edge 27, circumferential seal 42 is forcibly urged into sealing engagement with sealing surface 45 so as to elastically deform seal 42 and/or surface 45 such that, as nodes 40 pass over proximal edges 27 and into local recesses 29, seal 42 maintains sufficient pressure against surface 45 to maintain a seal therebetween.

As shown in FIGS. 8 and 9, delivery tube connector 17 is received within nozzle connector 33, wherein delivery tube connector 17 provides a female connector and nozzle connector 33 provides a complementary, mating male connector. Each node 40 slidably engages within the respective receiving slot 23 provided within delivery tube 11 so as to engage delivery tube connector 17 and nozzle connector 33, and axially connect together tip 10 and nozzle 30. During mating engagement therebetween, nozzles 30 rotatably engage in interlocking relation with transverse portions 26 of respective receiving slots 23 by co-action of each node 40 in sliding engagement with proximal edge, or override surface, 27 and local recess 29. Circumferential resilient seal 42 is interposed between delivery tube connector 17 and nozzle connector 33. Seal 42 is sized for resilient compressible engagement between delivery tube connector 17 and nozzle connector 33 as the pair of nodes 40 are rotatably engaged with the respective override surfaces 27. Seal 42 is further sized for sealing relaxed compressible engagement as nodes 40 are received within local recess 29 during final assembly there between.

Figure 10:
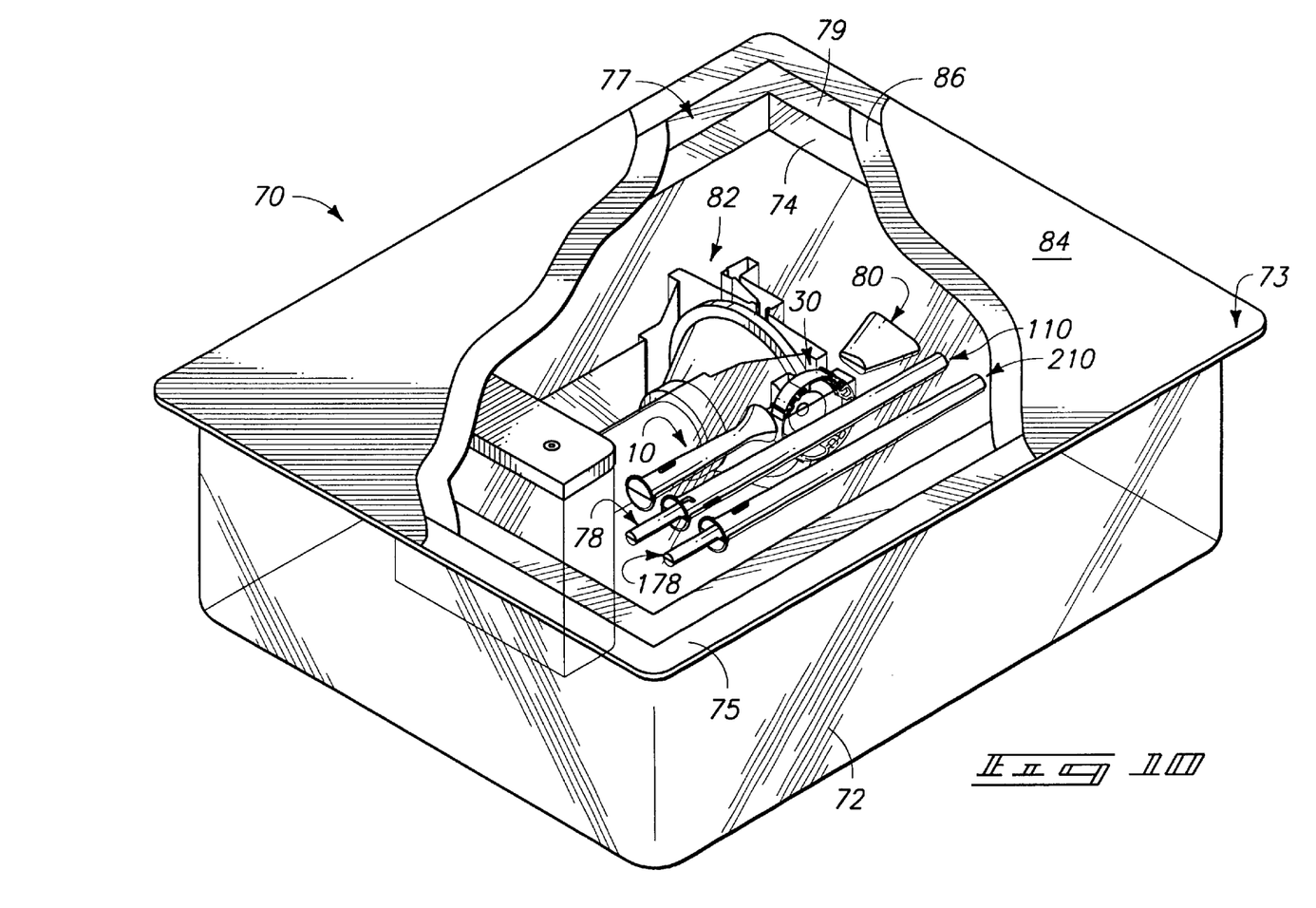
FIG. 10 is a perspective view of internested hermetically sealed tubs configured to store a plurality of interchangeable tips, the nozzle and other components of a bone cement delivery system.

FIG. 10 illustrates a tub assembly configured to store components of a bone cement delivery system 9 and generally indicated by reference numeral 70. Tub assembly 70 is formed by internested hermetically sealed tubs 72 and 74 that are configured to store one or more tips 10, 110, 210; a nozzle 30; and other components of a bone cement delivery system 9. Outer tub 72 includes a perimeter lip 73 on which a first seal 75 is secured over lip 73 of outer tub 72. An inner tub 74 is removably positioned inside outer tub 72 and includes a perimeter lip 77 on which a second seal 79 is secured over lip 77 of inner tub 74. Inner tub 74 houses various components of the bone cement delivery system 9 which were sterilized before being placed in inner tub 74 and hermetically sealed. The various components comprise: a plurality of tips 10, 110, 210; nozzle 30; clean out rods 78 and 178; proximal pressurizer 80; and mixer 82. Since tubs 72 and 74 are each individually hermetically sealed, first seal 75 can be removed in an environment less sterile than the surgical room; inner tub 74, still hermetically sealed, can be removed from outer tub 75 and placed in the surgical room. The second seal can be removed from the inner tub 74 as needed during the surgical procedure.

According to one construction, seals 75 and 79 are formed using plastic sheet material 84 and 86, respectively. One suitable sheet material 84 and 86 is formed using Tyvek®, a spunbonded olefin manufactured using very fine continuous filaments of highdensity polyethylene (HDPE). Such filaments are bonded together using heat and pressure. Tyvek® is manufactured and sold by E. I. du Pont de Nemours and Company, of Wilmington, Del. Tyvek® comprises a sterile packaging material suitable for forming a hermetic seal along seals 75 and 79.

According to one construction, tubs 72 and 74 are each formed from a clear material which enables a user to visually identify the various components of bone cement delivery system 9.

It should be appreciated that tips 10, 110, 210 may come in any number of shapes and designs. For example, FIGS. 1 and 7 illustrate a tip with a flared distal end. However, the distal ends could ;be cylindrical and slightly tapered similar to the tips shown located in inner tub 74 of FIG. 10. In one embodiment of the invention, three tips will be included in tub assembly 70 including one tip 110 wherein an axial bore approximates a diameter of 7 mm; another tip 210 wherein an axial bore approximates a diameter of 9 mm; and a flared tip 10 wherein the axial bore approximates a diameter of 9 mm.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A bone cement delivery apparatus, comprising:
   a delivery tube having an inner wall providing an axial bore; and
   a connector at a proximal end of the delivery tube including at least one receiving slot in the inner wall, a transverse portion of the receiving slot including an override surface and a local recess which cooperate to removably mate the delivery tube and the connector with a nozzle having a nozzle connector, the nozzle communicating with a container that receives a load of bone cement.

2. The delivery apparatus of claim 1 wherein the connector comprises a delivery tube connector, the nozzle connector is sized to engage with the delivery tube connector, the nozzle connector having an outer surface sized to be received in the axial bore of the delivery tube along the proximal end, the outer surface defining at least one node, the node configured to slidably engage within the receiving slot of the delivery tube so as to engage the delivery tube connector and the nozzle connector and axially connect together the tip and the nozzle.

3. The delivery apparatus of claim 2 wherein the nozzle is removably carried by the bone cement dispensing apparatus.

4. The delivery apparatus of claim 2 wherein the proximal end of the delivery tube comprises a frustoconical portion configured to receive the nozzle first portion.

5. The delivery apparatus of claim 4 wherein the receiving slot extends at least in part in an axial direction from the frustoconical portion towards a distal portion of the delivery tube.

6. The delivery apparatus of claim 5 wherein the receiving slot comprises an aperture formed between the inner wall and an outer wall of the delivery tube.

7. The delivery apparatus of claim 2 wherein the connector comprises a pair of diametrically opposed receiving slots, and the nozzle comprises a complementary pair of nodes, each node configured to slidably engage with one of the receiving slots.

8. The delivery apparatus of claim 7 wherein each complementary node of the nozzle is further configured to rotatably engage in interlocking relation with the transverse portion of a respective one of the receiving slots by coaction of each node in sliding engagement with the override surface and the local recess of the respective receiving slot.

9. The delivery apparatus of claim 8 wherein a resilient seal is interposed between the delivery tube connector and the nozzle, the seal sized for resilient compressible engagement between the delivery tube connector and the nozzle connector as the at least one node is rotatably engaged with the override surface, and further sized for sealing relaxed compressible engagement as the node is received within the local recess.

10. The delivery apparatus of claim 1 wherein the transverse portion comprises a cam surface, the node comprises a follower, and the local recess provides a locally stable interlocking surface for the follower operative to releasably engage the delivery tube with the nozzle on the bone cement dispensing apparatus.

11. The delivery apparatus of claim 1 wherein the receiving slot comprises an aperture provided in the tubular wall along the proximal end of the delivery tube, at least part of the aperture extending axially from the proximal end to the distal end.

12. The delivery apparatus of claim 1 wherein the outer wall of the delivery tube further comprises a plurality of radially extending ridges configured to facilitate tactile manipulation of the delivery tube and connector when mating/demating the delivery tube with the bone cement dispensing apparatus.

13. The delivery apparatus of claim 1 wherein the distal end of the delivery tube comprises a frustoconical endportion.

14. The delivery apparatus of claim 1 wherein the connector is integrally formed from the distal end of the delivery tube.

15. The delivery apparatus of claim 1 wherein at least a portion of the delivery tube has a progressively decreasing axial bore extending from the proximal end towards a distal end.

16. The apparatus of claim 1 wherein the nozzle comprises:

a first portion and a second portion, the first portion having an outer surface contoured to be received in a delivery tube, the outer surface defining at least one node configured to secure the delivery tube in interlocking engagement with the nozzle, and the second portion communicating with a supply of bone cement.

17. The nozzle of claim 16 wherein the first portion comprises a cylindrical outer surface and a circumferential seal integral with the cylindrical outer surface.

18. The nozzle of claim 17 wherein the circumferential seal rises above the cylindrical outer surface approximately 0.0025 inches.

19. The nozzle of claim 16 wherein the second portion is integral with the first portion, and the second portion is configured to mate with a bone cement container.

20. The delivery apparatus of claim 1 wherein the delivery tube has an axial bore of constant dimension from the proximal end toward a distal end.

21. The delivery apparatus of claim 1 wherein the circumferential seal extends radially outwardly of the cylindrical outer surface for a distance sufficient to form a fluid impermeable seal between the nozzle and the delivery tube.

22. A fluent material delivery apparatus, comprising:

a tip having a delivery tube and a delivery tube connector, the delivery tube connector including at least one receiving slot provided in the delivery tube and having a transverse portion including an override surface and a local recess; and a nozzle having a nozzle connector, the nozzle communicating with a fluent material dispensing apparatus and the nozzle connector configured to removably mate with the delivery tube, connector, the nozzle connector including at least one node sized for slidable engagement with the receiving slot and operative to mate in interlocking engagement within the local recess of the transverse portion responsive to circumferential manipulation of the nozzle and the at least one node over the override surface of the at least one receiving slot.

23. The delivery apparatus of claim 22 herein the nozzle connection comprises an outer surface contoured to be received in a proximal end of the delivery tube, the outer surface defining at least one node, the node having lateral walls extending from the outer surface to engage the receiving slot of the delivery tube to removably mate with the tip to the nozzle.

24. The delivery apparatus of claim 23 wherein the receiving slot comprises an aperture extending between an inner surface and an outer surface of the delivery tube, wherein the node is slidably received in the aperture during mating of the tip and the nozzle.

25. The delivery apparatus of claim 22 wherein the nozzle connector comprises a cylindrical outer surface and a circumferential seal integral with the cylindrical outer surface.

26. The delivery apparatus of claim 25 wherein the circumferential seal extends radially outwardly of the cylindrical outer surface approximately 0.0025 inches.

27. The delivery apparatus of claim 22 wherein the delivery tube connector comprises a pair of diametrically opposed receiving slots, and the nozzle comprises a pair of diametrically opposed, complementary nodes, each node configured to slidably engage with one of the receiving slots.

\* \* \* \* \*